United States Patent

Wickbold et al.

[11] 4,222,823
[45] Sep. 16, 1980

[54] METHOD FOR PROCESSING CHLORINATED HYDROCARBON RESIDUES

[75] Inventors: Reinhold Wickbold; Wolfgang H. E. Müller; Hans Regner; Günter Scharein; Franz Langheim; Rolf Ruthemeier; Karl-Hans Simmrock; Rolf Baumann, all of Marl, Fed. Rep. of Germany

[73] Assignee: Chemische Werke H',uml/u/ ls Aktiengesellschaft, Marl, Fed. Rep. of Germany

[21] Appl. No.: 720,356

[22] Filed: Sep. 3, 1976

[30] Foreign Application Priority Data

Sep. 10, 1975 [DE] Fed. Rep. of Germany ....... 2540178

[51] Int. Cl.$^2$ .......................... B01D 1/22; C01B 7/08; C10B 57/04
[52] U.S. Cl. .................................... 201/2.5; 159/6 W; 201/25; 202/209; 423/449; 423/481; 423/488
[58] Field of Search ..................... 201/2.5, 25; 48/111, 48/209; 423/488, 481; 159/6 W

[56] References Cited

U.S. PATENT DOCUMENTS

| | | | |
|---|---|---|---|
| 3,625,273 | 12/1971 | Buschor | 159/6 W |
| 3,716,339 | 2/1973 | Shigaki et al. | 201/25 X |
| 3,829,558 | 8/1974 | Banks et al. | 201/25 X |
| 3,832,151 | 8/1974 | Kitaoka et al. | 48/111 |
| 3,933,989 | 1/1976 | Itoh et al. | 423/488 |

*Primary Examiner*—Joseph Scovronek
*Attorney, Agent, or Firm*—Gilbert L. Wells

[57] ABSTRACT

The processing of liquid chlorinated hydrocarbon residues, which may contain solids and which form viscous to solid deposits during the separation of readily boiling components, into (1) distillable organic components,
(2) hydrogen chloride, and
(3) solid matter with a low chlorine content, is improved by gently concentrating the residues in a first step and, in a second step, decomposing the residues at temperatures of about 200°–400° C., preferably 270°–330° C., with a continuous separation of the vapor phase components from the solid components.

11 Claims, 2 Drawing Figures

METHOD FOR PROCESSING CHLORINATED HYDROCARBON RESIDUES

BACKGROUND OF THE INVENTION

The present invention relates to a method and apparatus for the processing of liquid chlorinated hydrocarbon residues which may contain solids and which form, when readily boiling components are separated, viscous to solid deposits. Such residues are obtained, for example, in the manufacture of vinyl chloride by the thermal cracking of 1,2-dichloroethane.

It is necessary to work up these residues of chlorinated hydrocarbons, since the dumping or combustion of these products causes ever increasing difficulties and, in part, is prohibited by law.

The state of the art processes producing liquid chlorinated hydrocarbon residues may be ascertained by reference to the Kirk-Othmer "Encyclopedia of Chemical Technology," Vol. 5 (1964), pp. 85-303, under the chapter "Chlorocarbons and Chlorohydrocarbons," particularly pps. 149-154, under the section "1,2-Dichloroethane," and pp. 171-175, under the section "Vinyl Chloride" and by reference to Stanford Research Institute, Report No. 5, pp. 50-68 and pp. 87-109, Report No. 5 A, pp. 59-72 and pp. 79-81, and Report No. 5 B, pp. 68-157 and pp. 158-163. All of the disclosures are incorporated herein to show the state of the art of 1,2-dichloroethane, vinyl chloride and the residues produced in the manufacture of these compounds and other liquid chlorinated hydrocarbons.

The state of the art of apparatus used in concentrating the residues may be ascertained by reference to Ullmann "Encyclopädie der technischen Chemie" 4. Auflage (1972) Vol. 2 pp. 652-661, particularly pp. 656-657.

One of the important prerequisites for placing a commercial chlorinated hydrocarbon plant on stream nowadays, in many areas, is the elimination of the by-products formed by a procedure harmless to the environment. Furthermore, the economy of the entire process is improved by obtaining usable substances from this waste.

Processes for the elimination of the chlorinated hydrocarbon residues which are truly satisfactory in meeting the aforementioned requirements have not been known heretofore. In a number of instances, residues from chlorinated hydrocarbons are deposited in more or less suitable locations, for example on the bottom of the sea. In specific cases, it is also possible to convert by-products of chlorinated hydrocarbon syntheses with the aid of chlorine to highly chlorinated products, such as carbon tetrachloride and perchloroethylene.

It is furthermore conventional to eliminate the chlorinated hydrocarbon residues by combustion. In the case of a high chlorine content, fuel oil or other fuels are added to make combustion possible. In more recent times, special burn ships have been put into operation which burn the chlorinated hydrocarbon waste on the open sea where the hydrogen chloride produced has a less severe impact on the environment. West German published patent application No. 1,228,232 of Arno Czekay et al. filed Jan. 24, 1964, and having a publication date of Nov. 10, 1966 is incorporated herein to show an improved procedure for a simple combustion, wherein the hydrogen chloride formed is absorbed from the combustion gases in a conventional manner.

Except for the procedure of depositing the waste, which is harmful to the environment, the above-described conventional methods are suitable merely for liquid products which do not contain any appreciable solids proportions and furthermore do not tend to cake or resinify. In particular, the residues from the vinyl chloride production by way of 1,2-dichloroethane and the thermal cracking thereof contain solids and moreover assume a viscous, tacky phase when concentrated and simultaneously subjected to the separation of readily boiling components. These properties exclude, for example, the processing of these residues in accordance with the prior art methods.

From the viewpoint of environmental protection, the methods of depositing and simple combustion are completely unsatisfactory. Moreover, considerable expenses are incurred by the transportation of the combustion ship at sea and/or for the waste depositing procedure. Positive factors cannot be listed for these prior art procedures. The installation and maintenance of a controlled depositing system and/or of a combustion ship furthermore require a considerable cost expenditure.

The process according to West German published application No. 1,228,232, concerning the combustion of chlorine containing products and the absorption of the hydrogen chloride formed from the combustion gases, can be viewed in a more favorable light than other methods with respect to the problems of environmental protection. However, the application of this process is restricted to readily fluid substances. Besides, the process exhibits the disadvantage that no useful materials are gained therefrom except for the hydrogen chloride. Particularly as encountered in combustion processes, this method likewise includes the drawback that strong corrosion occurs on all customary materials due to the presence of moist hydrogen chloride.

SUMMARY OF THE INVENTION

Having in mind the limitations of the prior art, it is an object of the present invention to process chlorinated hydrocarbon residues, optimally while recovering economically utilizable materials, while satisfying the requirements of environmental protection. The process of the present invention is specifically directed to chlorinated hydrocarbons which may contain solid matter and which attain a viscous and tacky condition during the evaporation of a portion of the residues, as required for obtaining readily boiling components. Among this type of residues are those produced during the manufacture of vinyl chloride by way of 1,2-dichloroethane.

The objects have been attained according to the present invention, considering the requirements in connection with environmental protection and with a relatively minor expenditure in apparatus and energy, in an economical way by subjecting the aforementioned residues to a combination of concentration and thermal decomposition with the exclusion of air. The residues are gently concentrated in a first stage and then thermally decomposed, with the exclusion of air in a second stage, while continuously separating the vapor phase components from the solid components.

According to the present invention, liquid chlorinated hydrocarbon residues, which may contain solids and which form viscous to solid deposits during the separation of readily boiling components, into distillable organic components, hydrogen chloride, and solid matter of a low chlorine content, are gently concentrated in a first step and decomposed in a second step at temperatures of about 200°–400° C., preferably 270°–330° C., while continuously separating the vapor phase components from the solid components.

BRIEF DESCRIPTION OF THE DRAWINGS

The present invention may be carried out in apparatus shown in the appended drawings having two embodiments detailed therein, in which.

DESCRIPTION OF THE PREFERRED EMBODIMENTS

Figure 1:
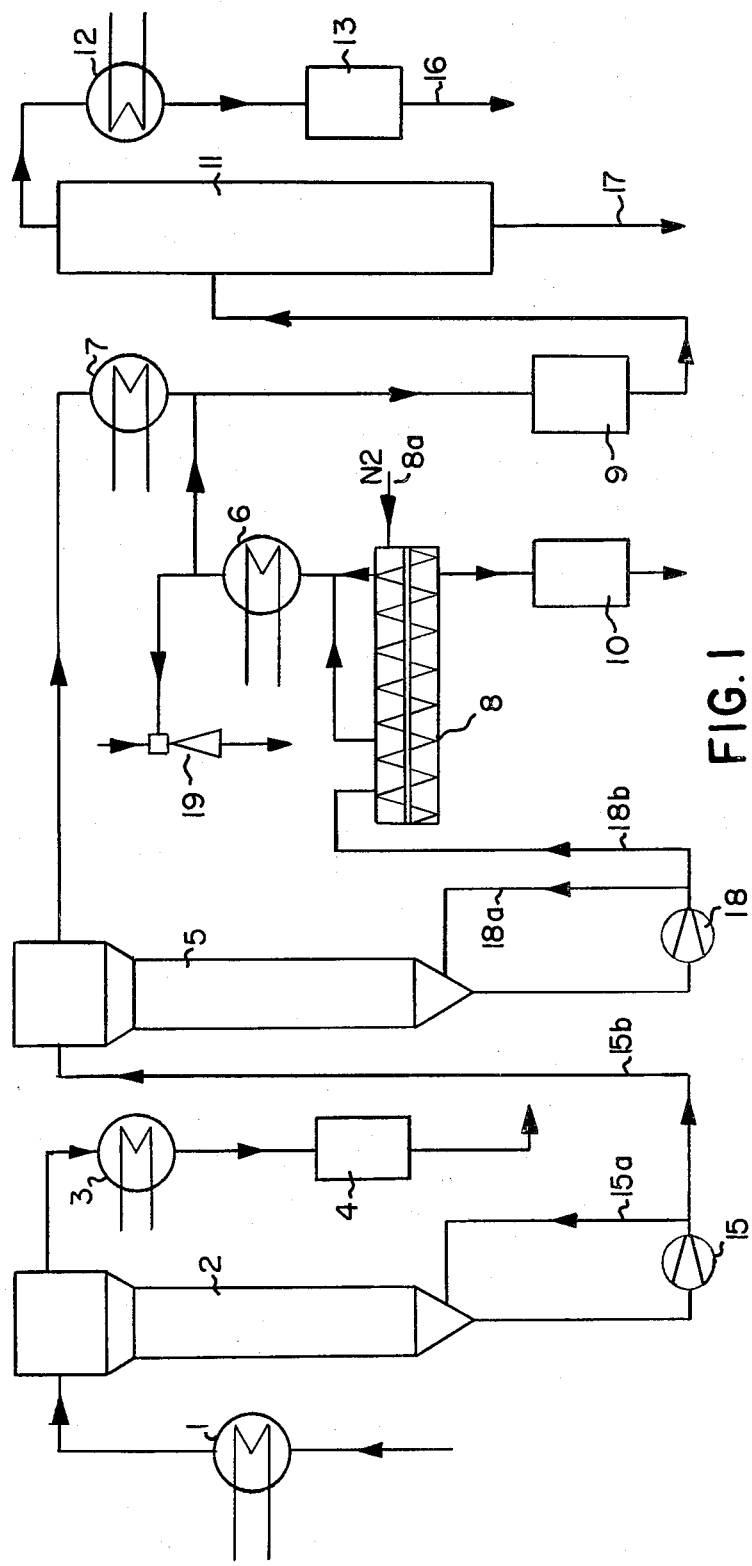
FIG. 1 is a flow diagram of an apparatus useful in the present invention showing evaporators for carrying out the first stage and a heated, self-cleaning screw-type apparatus for carrying out the second stage.

With particular reference to FIG. 1, a residue mixture is fed to heat exchanger or preheater 1 and after preheating to 75° C. is fed to agitated thin-film evaporator 2. A agitated thin-film evaporator useful in the present invention is disclosed in Ullmann "Encyclopädie der technischen Chemie" 4. Auflage (1972) Vol. 2 pp. 656–657. The low boiling component from evaporator 2 is condensed in heat exchanger or condenser 3, collected in receiver 4 and fed by line 14 to the distillation stage of a 1,2-dichloroethane production apparatus such as disclosed in Ullmann "Encycloädie der technischen Chemie" 4. Auflage (1972) Vol. 9 p. 448.

The higher boiling component in the sump of evaporator 2 is recycled by pump 15 through line 15a and a portion of the higher boiling component is conducted by line 15b to a second agitated thin-film evaporator 5.

The lower boiling component of evaporator 5 is condensed in heat exchanger or condenser 7 and collected in receiver 9. The vapors collected in receiver 9 are rectified in distillation column 11. The head product of column 11 is condensed by heat exchanger or condenser 12 and collected in receiver 13. The material collected in receiver 13 is introduced by line 16 into the working-up unit for the cracking gas of a 1,2-dichloroethane pyrolysis.

The sump product of column 11 is directed by line 17 to perchlorination reactions such as disclosed in Stanford Research Institute, Report No. 48, pp. 157–193.

The sump product of evaporator 5 is circulated by pump 18 for recirculation through line 18a and a portion is delivered by line 18b into heated, self-cleaning screw-type apparatus 8. The heated, self-cleaning screw-type apparatus having successive zones is particularly disclosed in Ullmann "Encyclopädie der technischen Chemie," 4. Auflage (1972) Vol. 2 p. 659 and West German published patent applications Nos. 1,194,765 and 1,653,872.

Vapors from screw-type apparatus 8 are condensed by heat exchanger or condenser 6 and also collected in receiver 9. A mixture of noncondensed gases passing through exchanger 6 without condensation is removed by aspirator 19. A residue from screw-type apparatus 8 is collected in tub 10 and from there is burned in the power plant.

Figure 2:
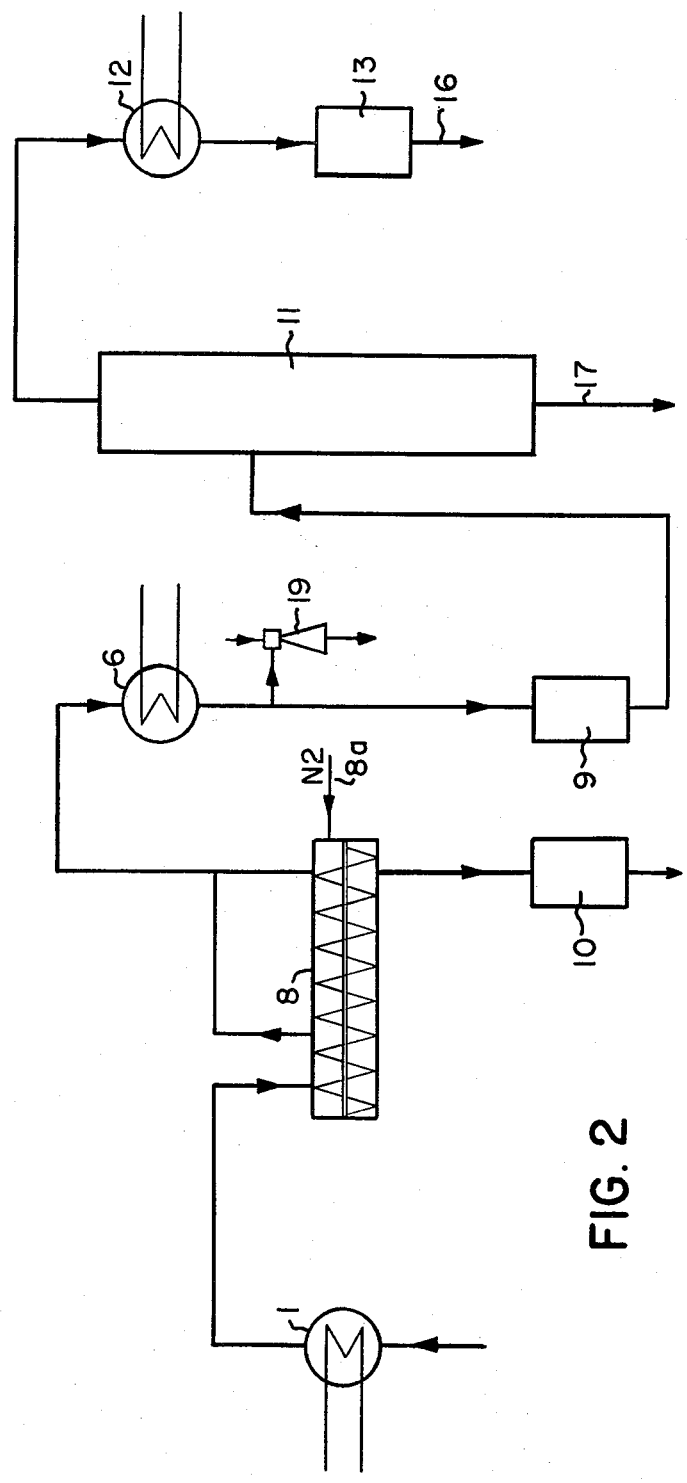
FIG. 2 is a flow diagram of an apparatus useful in the present invention showing a heated, self-cleaning screw-type apparatus for carrying out both stages.

FIG. 2 illustrates the embodiment of the apparatus wherein both stages of the present invention are carried out in successive zones of the heated, self-cleaning screw-type apparatus.

A residue mixture is introduced into the system through heat exchanger or preheater 1 and from there is conducted to heated, self-cleaning screw-type apparatus 8. Nitrogen is introduced into the far end of screw-type apparatus 8 at 8a. Vapors mixed with nitrogen from the screw-type apparatus 8 are cooled and the vapors condensed in heat exchanger 6. HCl mixed with nitrogen is removed by aspirator 19 and the condensed vapors are rectified in column 11. Carbon black containing residue is collected in tub 10 and burned in the power plant. The head product of column 11 is condensed by heat exchanger or condenser 12 and collected in receiver 13. The material collected in receiver 13 is introduced by line 16 into the working-up unit for the cracking gas of a 1,2-dichloroethane pyrolysis. The sump product of column 11 is directed by line 17 to perchlorination reactions.

The residues to be treated generally consist of carbon black, inorganic compounds, low- and high-molecular, saturated and unsaturated chlorinated hydrocarbons. The readily boiling components are primarily the following

|  | Boiling Point |
| --- | --- |
| Vinyl chloride | −14° C. |
| Vinylidene chloride | +32° C. |
| Trans-Dichloroethylene | +48° C. |
| 1,1-Dichloroethane | +57° C. |
| Cis-Dichloroethylene | +60° C. |
| Chloroform | +61° C. |
| 1,1,1-Trichloroethane | +74° C. |
| 1,2-Dichloroethane | +83° C. |

Thin-film evaporators are particularly suitable for the first process step, namely the concentration of the residues, because these devices ensure an extensively gentle treatment of the feed stock from a thermal viewpoint. This is required since the higher chlorinated hydrocarbons, e.g. 1,1,2-trichloroethane, contained in the chlorinated hydrocarbon residues are thermally unstable and form deposits during their decomposition. These deposits lead, in presently used evaporators, to encrustations which lower the operating periods for the devices and increase the costs for cleaning operations.

To ensure over the entire process step of the evaporation a fluid product mixture, on the one hand, but to prevent, on the other hand, the transfer of too great a quantity of valuable distillable organic components into the economically less favorable decomposition stage in the second process step, the residues which contain the chlorinated hydrocarbons are evaporated, for example in a thin-film apparatus, to such an extent that a mixture remains having a viscosity of 8–50 cp., preferably 10–15 cp. at 20° C. and at a shear velocity of 200 sec.$^{-1}$. The indicated values relate to measurements with a Couette viscosimeter. The vapors obtained in the evaporation are condensed. The condensate is separated into its components by a rectifying distillation process and these components are recycled into chemical processes. The condensate can also be used, in a cycle-type procedure, for the dilution of substance mixtures to be worked up which otherwise could not be transported. The 1,2-dichloroethane recovered by distillative separation can be used, for example, for the manufacture of vinyl chloride. The other chlorinated hydrocarbons can be used for the production of perchloroethylene.

Depending on the quantity of residues obtained, the evaporation can be carried out in one or in several thin-film evaporators. In this connection, the evaporators can not only be operated in parallel but also in a series connection. The evaporation residues obtained in the sumps of the thin-film evaporators are conducted by means of pumps into the subsequent evaporator and/or into the second process stage. In this connection, it is advantageous to dimension the pump power in such a way that a multiple of the amount of the sump runoff is recycled into the sump, i.e. recirculated by the pumps. This measure provides a sufficient homogenization of the individual product streams and prevents interruptions in operation due to the necessary cleaning of clogged conduits. In general, it has proved to be advantageous to recycle 3- to 10-times the amount of the sump runoff into the sump.

The residue of low- and high-molecular, saturated and unsaturated chlorinated hydrocarbons concentrated in the first process stage and including carbon black and inorganic compounds is subjected in the second stage to a further evaporation and to a thermal decomposition. This process step is conducted at temperatures of 200°–400° C., preferably at temperatures of 270°–330° C. The thermal decomposition is generally conducted in a heated apparatus from which the decomposition products are withdrawn. Preferably, a continuously operating, heated, self-cleaning screw-type device is utilized.

The thermal decomposition is extended so that a carbon black remains containing less than 10 percent of chlorine as the final product of the processing of liquid chlorinated hydrocarbon residues. The carbon black is conveyed from the decomposition apparatus into a tub and is then readily combusted, e.g. mixed with coal, with energy gain.

The carbon formed in the second process stage is an excellent adsorbent, inter alia also for chlorinated hydrocarbons. Therefore, it is advantageous to prevent an effect of the liberated vapors on the thus-formed carbon at a lower temperature. This is accomplished during the second process step in accordance with the present invention by maintaining a gaseous flow in opposition to the product stream. The gaseous flow can be effected by the application of a sufficient vacuum and/or by the introduction of an inert gas stream into the decomposition unit. Preferably, nitrogen is employed as the inert gas.

The vapors of the second stage can optionally be subjected, together with those of the first stage, to a rectifying distillation procedure.

The entire process, namely concentration and thermal decomposition of the chlorinated hydrocarbon residues can also be conducted in a worm-type apparatus if the amount of the residues to be processed is relatively small. A requirement in this connection is that the size of the heat exchange surface area be in a specific proportion to the quantity of chlorinated hydrocarbon residues to be worked up.

The process of the present invention makes it possible to process chlorinated hydrocarbon residues which heretofore did not lend themselves satisfactorily to processing in accordance with other, conventional processes. The method can be employed in the case of residues which contain greater or lesser amounts of solids, and which form viscous and/or tacky deposits during concentration, thus leading to the clogging of installations.

The process of the present invention does not yield any substances which cannot be used and which would have to be dumped. The substances obtained therefore are beneficial factors which improve the economy of the method during which the residues were obtained. The process can be conducted fully continuously and with automation.

Specific examples of the process are set forth as follows:

EXAMPLE 1

(See FIG. 1 of the drawing)

Four tons per hour of a residue mixture containing, in addition to carbon black, inorganic compounds, low- and high-molecular, saturated and unsaturated chlorinated hydrocarbons, inter alia furthermore vinyl chloride, 1,1-dichloroethylene, trans- and cis-dichloroethylene, 1,1-dichloroethane, chloroform, 1,1,1-trichloroethane, and 1,2-dichloroethane and from the 1,2-dichloroethane cleavage into vinyl chloride and HCl, is fed to a thin-film evaporator 2 after being heated in a preheater 1 to 75° C. Two tons per hour (=50 percent of the feed) is evaporated from the thin-film unit, exposed to low pressure steam. After being subjected to condensation in unit 3, the reaction mixture is introduced via valves by way of a receiver 4 into the distillation processing stage of the cracking gas mixture of the 1,2-dichloroethane pyrolysis. The two tons per hour remaining in the sump of the thin-film evaporator 2 is conducted through line 15b with the aid of pump 15, while recycling 10 tons per hour through line 15a into the sump of the thin-film evaporator 2, into a further thin-film evaporator 5 which is likewise heated with low pressure steam. An amount of 1.2 tons per hour is evaporated, condensed in 7, and collected in a receiver 9. The sump of the thin-film evaporator 5, which is still of satisfactory fluidity (evaporation residue at 120° C.=30 percent, quantity=0.8 ton per hour, with a viscosity of 11 cp. at 20° C. and a shear velocity of 200 sec.$^{-1}$ measured with a Couette viscosimeter), is pumped by pump 18 through line 18b into a heated, self-cleaning screw-type apparatus 8 wherein 4 tons per hour is recycled through line 18a into the sump of the thin-film evaporator 5. In the screw-type apparatus 8, charged with a thermal oil, the sump runoff from the thin-film evaporator 5 is thermally decomposed by being brought to a temperature of 300° C. under a stream of nitrogen flowing thereover from line 8a. A residue (0.04 ton per hour) with a high carbon black content and with 8–10 percent of chlorine is thus obtained in the tub 10 and this residue is combusted in the power plant while gaining energy. The vapors of the screw-type device (about 0.76 ton/hour), consisting of 1,2-dichloroethane and decomposition products, such as the isomeric dichloroethylenes, are condensed in the heat exchanger 6 and likewise collected in the receiver 9. The mixture of inert gas and chlorinated hydrocarbon (HCl~5 kg/h) which has not been condensed in condenser 6 is removed under suction with the aid of a water jet aspirator downstream of unit 6. The vapors collected in the receiver 9 (about 1.955 ton/hour) of the second thin-film evaporator 5 and the screw-type unit 8 are rectified in the distillation column 11. The head product from unit 11 (1.75 ton/hour), containing primarily 1,2-dichloroethane and the isomeric dichloroethylenes, is introduced via a heat exchanger 12, a receiver 13 and line 16 into the working-up unit for the cracking gas of the 1,2-dichloroethane pyrolysis. The sump product (0.205 ton/hour) of the column 11, consisting predominantly of higher chlorinated hydrocarbons (especially 1,1,2-trichloroethane), is utilized in perchlorination reactions through line 17.

EXAMPLE 2.

(See FIG. 2 of the Drawing)

Two tons per hour of a residue mixture as described in Example 1 is introduced, after heating in a preheater 1° to 75° C., into a heated, self-cleaning screw-type apparatus 8 and worked up therein as disclosed in Example 1. In the tub 10, about 0.02 ton/hour of a carbon black containing residue is collected. Vapors amounting to 1.98 ton/hour escape from the screw-type heater 8, consisting of 1,2-dichloroethane and decomposition products of the higher chlorinated hydrocarbons which, after condensation and cooling in the heat exchanger 6, and after passing through the receiver 9, are subjected to the largest part to a rectifying distillation in column 11. About 2-3 kg/h of hydrogen chloride is removed by suction with a water-jet aspirator 19 in a mixture with nitrogen at a point downstream of unit 6. Approximately 1.877 ton/hour is obtained as the head product of column 11 at 16 and 0.1 ton/hour is produced as the sump runoff 17.

We claim:

1. In the method for the processing of liquid chlorinated hydrocarbon residues containing solids and forming viscous to solid deposits during the separation of readily boiling components into
   (1) distillable organic components,
   (2) hydrogen chloride, and
   (3) solid matter with a low chlorine content
the improvement comprising gently concentrating said liquid chlorinated hydrocarbon residues in a first process step, removing concentrated residues and decomposing in a second process step said concentrated residues at temperatures of about 200°-400° C., followed by continuously separating the vapor-phase components from the solid components.

2. The method of claim 1, wherein said first process step is conducted in a thin-film evaporator.

3. The method of claim 2, wherein 3 to 10 times the amount of the sump runoff is recycled into the sump of the thin-film evaporator.

4. The method of claim 3, wherein said residues are concentrated to a viscosity of 8-50 cp at 20° C. and a shearing velocity of 200 sec.$^{-1}$.

5. The method of claim 1, wherein said second process step is conducted in a continuously operating, heated, self-cleaning screw-type apparatus.

6. The method of claim 5, wherein said second process step is conducted in the presence of an inert gas.

7. The method of claim 6, wherein said inert gas is a gaseous stream conducted counter-currently to the product to be worked up.

8. The method of claim 7, wherein nitrogen is said inert gas.

9. The method of claim 1, wherein both process steps are conducted in successive zones of a heated, self-cleaning screw-type apparatus.

10. The method of claim 1, wherein said second process step is carried out at temperatures of about 270°-330° C.

11. The method of claim 4, wherein said viscosity is 10-15 cp at 20° C.

* * * * *